(12) United States Patent
Fronda et al.

(10) Patent No.: US 10,849,786 B2
(45) Date of Patent: Dec. 1, 2020

(54) HEADWEAR FOR REMOVING HEAT FROM A PERSON'S SCALP IN ORDER TO PREVENT HAIR LOSS

(75) Inventors: Carl Frank Fronda, London (GB); Darren Lee Fronda, London (GB)

(73) Assignees: Frank Derek Fronda, London (GB); Carl Frank Fronda, London (GB); Darren Lee Fronda, London (GB)

( * ) Notice: Subject to any disclaimer, the term of this patent is extended or adjusted under 35 U.S.C. 154(b) by 414 days.

(21) Appl. No.: 13/261,794

(22) PCT Filed: Jun. 26, 2012

(86) PCT No.: PCT/GB2012/000548
§ 371 (c)(1),
(2), (4) Date: Jan. 7, 2014

(87) PCT Pub. No.: WO2013/007964
PCT Pub. Date: Jan. 17, 2013

(65) Prior Publication Data
US 2014/0236271 A1    Aug. 21, 2014

(30) Foreign Application Priority Data
Jul. 8, 2011    (GB) .................................. 1111717.3

(51) Int. Cl.
*A61F 7/10*    (2006.01)
*A61F 7/00*    (2006.01)
*A61F 7/02*    (2006.01)

(52) U.S. Cl.
CPC ........ *A61F 7/10* (2013.01); *A61F 2007/0008* (2013.01); *A61F 2007/0056* (2013.01);
(Continued)

(58) Field of Classification Search
CPC ............................................... A61F 2007/0008
See application file for complete search history.

(56) References Cited

U.S. PATENT DOCUMENTS 3,786,805 A * 1/1974 Tourin ................ A61F 5/05816
128/DIG. 20
4,035,846 A * 7/1977 Jencks ................... A42B 3/122
2/413

(Continued)

FOREIGN PATENT DOCUMENTS

| GB | 1 462 033 | 1/1977 |
|---|---|---|
| WO | WO 00/03666 | 1/2000 |
| WO | WO 2005/028984 | 3/2005 |

*Primary Examiner* — Kaitlyn E Smith
(74) *Attorney, Agent, or Firm* — Iandiorio Teska & Coleman, LLP

(57) ABSTRACT

Headwear (2) for removing heat from a person's scalp in order to prevent hair loss, comprising a body portion (4) for fitting over the scalp, an inlet (6) and an outlet (8), and fastener means (10) the headwear (2) being such that it opens to a flat condition when it is not in use on the person's head (12), and the body portion (4) comprises a plurality of internal walls (14) which define a passageway (18) through the body portion (4) from the inlet (6) to the outlet (8) whereby the cold fluid is able to circulate through the body portion (4), and the passageways (16) being such that they are expanded by the cold fluid and press against the person's scalp with a pressure which causes contact with the person's scalp and thereby to facilitate maximum cold transfer.

16 Claims, 4 Drawing Sheets

(52) U.S. Cl.
CPC .............. *A61F 2007/0225* (2013.01); *A61F 2007/0273* (2013.01); *A61F 2007/0287* (2013.01)

(56) References Cited

U.S. PATENT DOCUMENTS

| | | | | |
|---|---|---|---|---|
| 4,138,743 | A * | 2/1979 | Elkins | A42B 3/285 2/171.2 |
| 4,566,455 | A * | 1/1986 | Kramer | A61F 7/10 2/171.2 |
| 4,691,762 | A * | 9/1987 | Elkins | A61F 7/02 165/46 |
| 5,342,411 | A * | 8/1994 | Maxted | A61F 7/00 607/107 |
| 5,603,728 | A * | 2/1997 | Pachys | A61F 7/02 607/104 |
| 5,871,526 | A | 2/1999 | Gibbs et al. | |
| 5,897,581 | A * | 4/1999 | Fronda | A61F 7/10 607/109 |
| 6,030,412 | A * | 2/2000 | Klatz | A61F 7/00 607/104 |
| 6,117,164 | A * | 9/2000 | Gildersleeve | A61F 7/02 607/108 |
| 6,178,562 | B1 * | 1/2001 | Elkins | A41D 13/005 2/102 |
| 6,197,045 | B1 * | 3/2001 | Carson | A61F 7/02 601/148 |
| 6,312,453 | B1 * | 11/2001 | Stefanile | A61F 7/10 607/108 |
| 6,551,347 | B1 * | 4/2003 | Elkins | A61F 7/0085 165/46 |
| 6,695,872 | B2 * | 2/2004 | Elkins | A41D 13/005 607/104 |
| 8,226,698 | B2 * | 7/2012 | Edelman | A61F 7/02 607/104 |
| 8,425,579 | B1 * | 4/2013 | Edelman | A61F 7/02 601/34 |
| 8,834,548 | B2 * | 9/2014 | Liang | A61F 7/0241 219/385 |
| 9,072,577 | B1 * | 7/2015 | Ferko, III | A61F 7/00 |
| 2002/0138033 | A1 * | 9/2002 | Elkins | A41D 13/005 604/6.13 |
| 2003/0078640 | A1 * | 4/2003 | Carson | A61F 7/0085 607/104 |
| 2004/0167594 | A1 * | 8/2004 | Elkins | A41D 13/005 607/108 |
| 2004/0243202 | A1 * | 12/2004 | Lennox | A61F 7/0085 607/104 |
| 2005/0065584 | A1 * | 3/2005 | Schiff | A61F 7/12 607/105 |
| 2005/0107855 | A1 * | 5/2005 | Lennox | A61F 7/10 607/104 |
| 2005/0221037 | A1 * | 10/2005 | Panyard | A61F 7/02 428/36.9 |
| 2007/0118194 | A1 * | 5/2007 | Mason | A61F 7/02 607/104 |
| 2008/0097560 | A1 * | 4/2008 | Radziunas | A61F 7/10 607/104 |
| 2008/0234788 | A1 * | 9/2008 | Wasowski | A43B 7/34 607/104 |
| 2008/0269852 | A1 * | 10/2008 | Lennox | A61F 7/02 607/104 |
| 2008/0312723 | A1 * | 12/2008 | Gill | A61F 7/12 607/105 |
| 2010/0030306 | A1 * | 2/2010 | Edelman | A61F 7/02 607/104 |
| 2010/0106229 | A1 | 4/2010 | Gammons et al. | |
| 2010/0137765 | A1 * | 6/2010 | Edelman | A61F 7/02 602/14 |
| 2010/0186436 | A1 * | 7/2010 | Stormby | A61F 7/10 62/259.3 |
| 2011/0008179 | A1 * | 1/2011 | Turner | A61M 1/0031 417/53 |
| 2011/0077605 | A1 * | 3/2011 | Karpowicz | A61M 1/0001 604/318 |
| 2011/0106023 | A1 * | 5/2011 | Lowe | A61F 7/02 604/291 |
| 2012/0089210 | A1 * | 4/2012 | Woodall | A61F 7/0053 607/104 |
| 2012/0130457 | A1 * | 5/2012 | Gammons | A61F 7/02 607/104 |
| 2012/0172955 | A1 * | 7/2012 | Dewaegenaere | A61F 7/02 607/104 |
| 2013/0138185 | A1 * | 5/2013 | Paxman | A61F 7/0085 607/104 |
| 2013/0211484 | A1 * | 8/2013 | Rozental | A42B 3/122 607/110 |
| 2014/0046410 | A1 * | 2/2014 | Wyatt | A61F 7/10 607/104 |
| 2014/0222121 | A1 * | 8/2014 | Spence | A41D 13/005 607/104 |
| 2016/0339156 | A1 * | 11/2016 | Gordon | A61M 1/0001 |
| 2018/0055721 | A1 * | 3/2018 | Quisenberry | A61F 7/02 |

* cited by examiner

HEADWEAR FOR REMOVING HEAT FROM A PERSON'S SCALP IN ORDER TO PREVENT HAIR LOSS

This invention relates to headwear for removing heat from a person's scalp in order to prevent hair loss.

Headwear is known for removing heat from a person's scalp in order to prevent hair loss. One known type of headwear is such that it is used on its own, having first been cooled to a required cold temperature, and then placed on the person's head. This type of known headwear is disclosed in our Patent PCT/GB95/02042.

The headwear may alternatively be such that a cold fluid, for example cold water, is circulated through the headwear. This type of known headwear needs to be associated with a source of the cold fluid, and also with a pump for pumping the cold fluid through the headwear. This type of headwear is often not satisfactory in that the headwear does not fit sufficiently tightly to the person's head in use, with the result that the headwear does not cool the person's scalp as efficiently as it should do.

It is an aim of the present invention to reduce the above mentioned problem with headwear of the type which requires the circulation of a cold fluid in use.

Accordingly, the present invention provides an apparatus for removing heat from an adult person's scalp solely in order to prevent hair toss, the apparatus comprising a one-piece item of headwear and a feed pump for pumping a cold fluid to the headwear, and wherein:
(i) the headwear comprises a body portion for fitting over the person's scalp, an inlet for the cold fluid, an outlet for the cold fluid, and fastener flaps which comprise matrices of hook or loop material and which fold over the headwear and adjustably releasably grip parts of the headwear for fastening the headwear securely on the person's head, wherein the headwear opens to a flat condition when it is not in use on the person's head, in the flat condition the flaps extend outwardly beyond the body portion, access to the person's heard scalp is not provided through the body portion, and the body portion comprises a plurality of internal wads which define pouch portions, the pouch portions being connected to one another to define a passageway through the body portion from the inlet to the outlet whereby the cold fluid is able to circulate through the body portion, at least some of the pouch portions being of dissimilar shapes, the pouch portions are expandable by the cold fluid with the expansion being restricted by the folded fastener flaps whereby the pouch portions are caused in use to press against the person's scalp with a pressure which causes the body portion to be pressed into good contact with the person's scalp and thereby to facilitate maximum cold transfer from the body portion to the person's scalp,
(ii) the feed pump comprises control means which is configured to operate to maintain in use a substantially constant pressure in the headwear and thereby a substantially constant pressure exerted by the headwear on the person's scalp, whereby the person wearing the headwear is able to stand up without causing a change in pressure in the headwear and resulting discomfort to the person wearing the headwear,
(iii) the control means comprises a pressure sensor located at the headwear, and
(iv) the control means and the pressure sensor are configured such that the apparatus operates only at the substantially constant pressure and only within a pressure range of 7-18 millibars.

The headwear is able to be used with a pressure which causes the body portion to be pressed into good contact with the person's scalp, whilst at the same time not being so great as to cause discomfort to the person. The pouch portions are able to be chosen to be of sizes which are not so small that they do not expand sufficiently in order to obtain the good contact with the person's scalp. Also, the pouch portions are able to be chosen of sizes such that they are not so large that they contain too much water, and thereby cause the headwear to become too heavy and uncomfortable for the person to wear.

Generally, the pouches are of a size and shape that enables them to inflate such that they apply a substantially even pressure on the person's scalp during use. For example if pouches to the sides of the headwear are too large, they become too heavy and deform the shape of the headwear. This excess weight of fluid causes the pouches on top of the headwear to flatten, restricting the flow of the cold fluid. Preferably, the pouches are chosen to be of a size such that the total cold fluid content in the headwear is approximately 1.6 Kg.

The headwear of the present invention operates to remove heat from the person's scalp. The removal of heat lowers the metabolic rate of the hair follicles in the scalp. The headwear reduces blood flow through the person's scalp by removing the heat which causes capillaries in the person's scalp to shrink in diameter and therefore provide less blood, and also by simultaneously exerting pressure on the capillaries which again reduces their diameter and thereby the amount of blood passing through them. The cold fluid is preferably water but it may be brine, a refrigerant or any other suitable and appropriate fluid.

The headwear may be one in which the headwear is formed of sheets of material, and in which the internal walls are formed by welding the sheets of material together. The welding may be ultrasonic welding, heat welding or any other suitable and appropriate desired form of welding.

The headwear may be one in which there are two of the sheets, the first sheet comprising a layer of a plastics material having a layer of a grippable material on an outer surface of the layer of the plastics material, the second sheet comprising a layer of plastics material which is thicker than the plastics material in the first sheet, and the two layers of the plastics material being in contact with each other.

The two layers of the plastics material will usually be two layers of the same plastics material, but they may be different if desired. A presently preferred plastics material is a urethane plastics material.

The grippable material is preferably a velouch material. The velouch material is like a nylon felt material.

The fastener flaps preferably comprise Velcro (Registered Trade Mark) material.

The headwear may be one in which the inlet is an inlet pipe which extends beyond the periphery of the headwear, and in which the outlet is an outlet pipe which extends beyond the periphery of the headwear.

The apparatus may include a drain pump for removing the cold fluid from the headwear. The control means may control the drain pump.

The control means maintains in use a substantially constant pressure in the headwear. Without the control means, the provision of a substantially constant pressure in the headwear can be difficult because the pressure varies if the person wearing the headwear moves. This is especially so if the person should stand and then sit down. The pressure would increase substantially and can cause discomfort to the person and/or rupture of the headwear. Thus the provision of control means which in use maintains a substantially constant pressure in the headwear is advantageous both for the patient in maintaining patient comfort, and also for the headwear in avoiding it rupturing and thus not being reusable with other persons.

The control means preferably includes a pressure sensor at the headwear to feed pressure information to a control board, and a flow restrictor.

The control means may operate to maintain a chosen substantially constant pressure within the range of 5-20 millibars. Preferably the substantially constant pressure is chosen to be one within the range of 9-17 millibars. A presently preferred constant pressure is 14 millibars.

The apparatus may include a device for removing heat from the fluid being passed through the headwear. This may be an insulated container containing ice, a peltier cooler, or a compressor-style refrigeration unit.

The apparatus of the invention may operate such that pressure in the headwear is maintained by a pump which pumps cold fluid, for example water, to the headwear faster than it can flow through the flow restrictor. This causes the headwear to fill with the cold fluid which will start to pressurise the headwear. The pressure sensor sends pressure information back to the control board so as to slow the pump down as the pressure increases. A point of equilibrium will then be established. The control means may be set so that this equilibrium point is preferably at 10 millibar.

The flow restrictor may be an adjustable flow restrictor or a fixed flow restrictor. It is preferably set/chosen to provide flow of 1 litre of fluid a minute when the headwear is at operational pressure.

A pressure release valve is preferably fitted so as to protect the headwear from overpressure damage. This could happen if the fluid flowing through the headwear was to be restricted.

Preferably, the apparatus is mobile apparatus for being movable by the person. This ensures that the person does not have to be static during treatment, which may last for substantial periods of time, for example over one hour.

The mobile apparatus may have wheels for enabling the mobile apparatus to be wheeled to a desired position.

Advantageously, the apparatus is battery powered. In the case of the mobile apparatus, then the person is easily able to move the apparatus to a desired position and is not constrained by the length of an electrical lead as would be the case if the apparatus were to be mains powered and plugged into an electrical socket. If desired however, the apparatus of the present invention may additionally or alternatively be mains powered.

Embodiments of the invention will now be described solely by way of example and with reference to the accompanying drawings in which.

Figure 1:
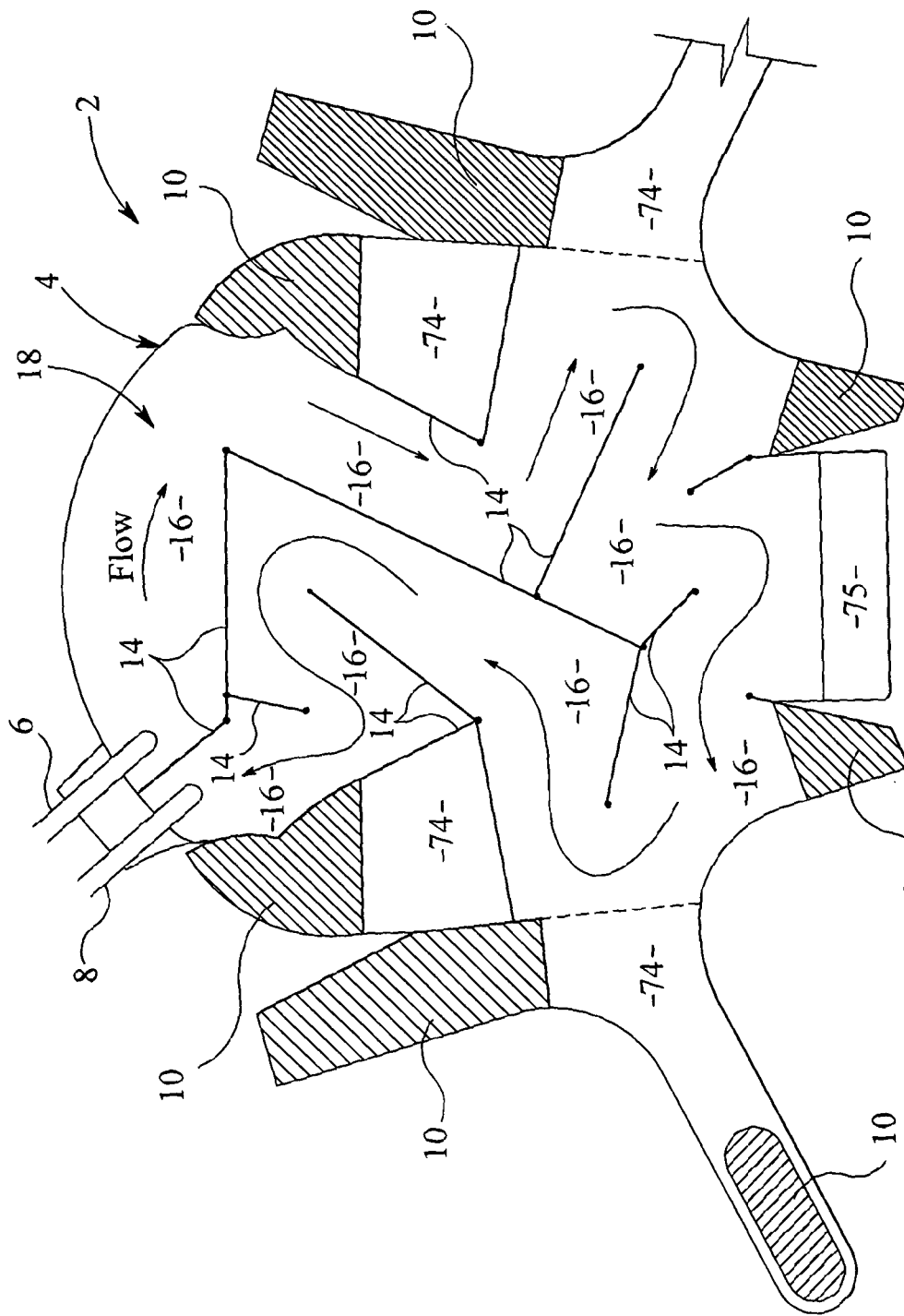
FIG. 1 shows headwear forming part of the present invention and in a flat condition when it is not in use on a person's head.
Figure 2:
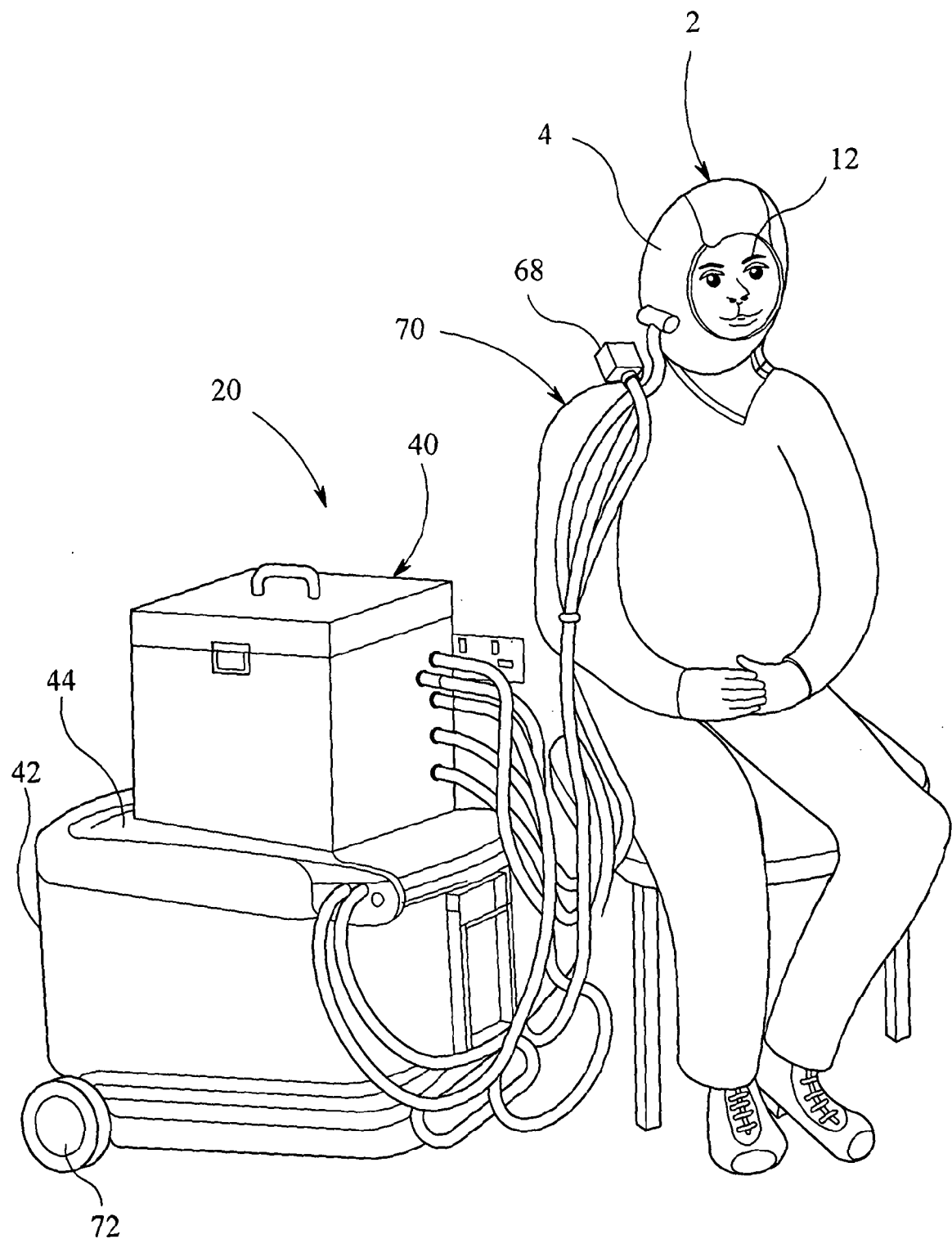
FIG. 2 shows the headwear of FIG. 1 in use on a person's head and with forming part of first apparatus.
Figure 3:
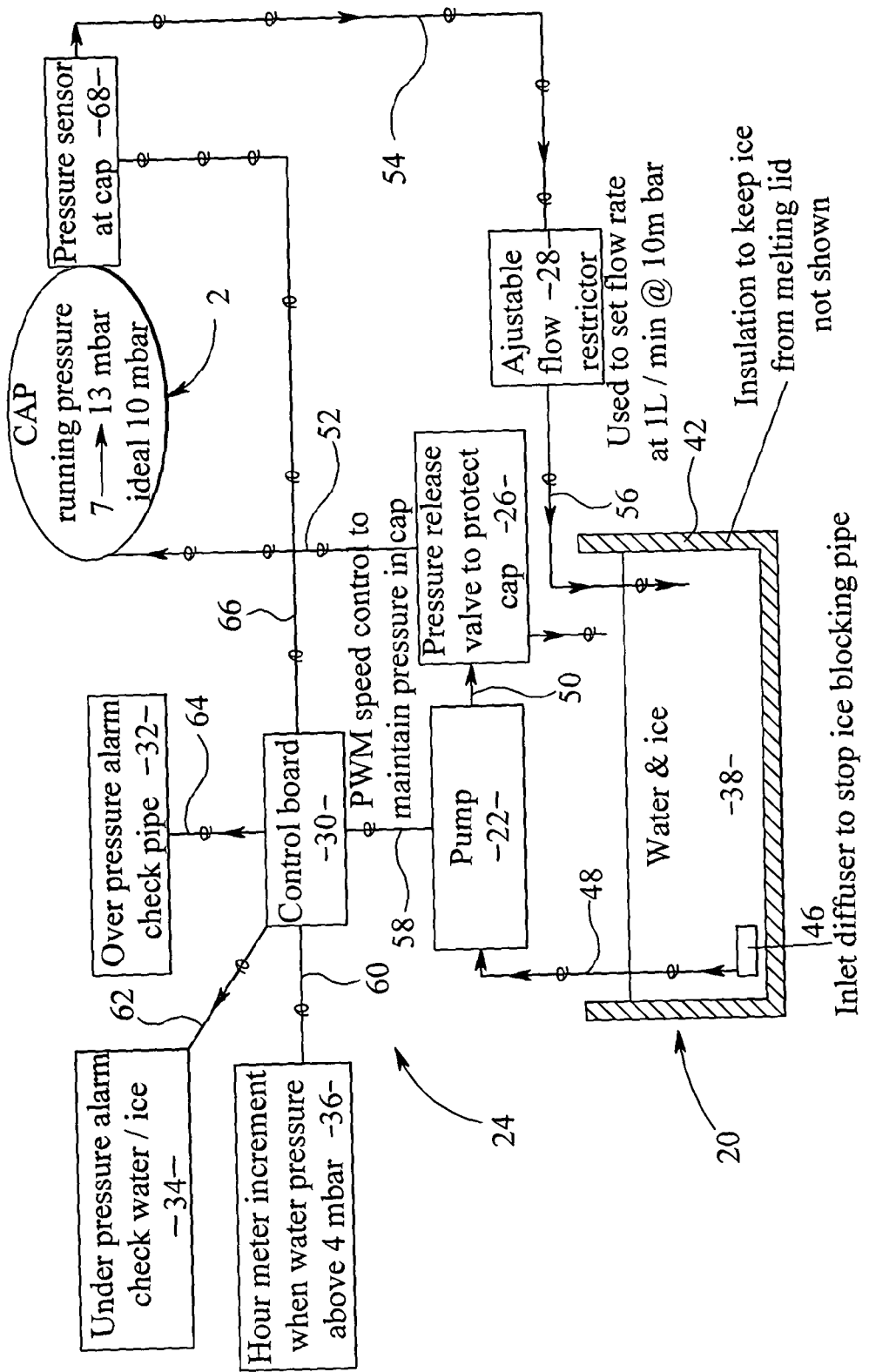
FIG. 3 illustrates the construction and operation of the first apparatus shown in FIG. 2.

Referring to FIGS. 1-3, there is shown headwear 2 for removing heat from a person's scalp in order to prevent hair loss. The headwear 2 comprises a body portion 4 for fitting over the person's scalp. The headwear 2 also comprises an inlet 6 and an outlet 8. The headwear 2 further comprises fastener means 10 for fastening the headwear 2 on the person's head 12.

The headwear 2 is such that it opens to a flat condition when it is not in use on the person's head. The flat condition is shown in FIG. 1. The use position on the person's head 12 is shown in FIG. 2.

As shown in FIG. 1, the body portion 4 comprises a plurality of internal walls 14 which define pouch portions 16. The pouch portions 16 are connected to one another as shown in FIG. 1 to define a passageway 18 through the body portion 4 from the inlet 6 to the outlet 8. A cold fluid is able to pass through the passageway 18 and thereby circulate through the body portion 4 as indicated by flow arrows in FIG. 1.

The pouch portions 16 are such that they are expanded by the cold fluid. This expansion causes the pouch portions 16 to press against the person's scalp with a pressure which causes the body portion 4 to be pressed into good contact with the person's scalp. This thereby facilitates maximum cold transfer from the body portion 4 to the person's scalp.

The internal walls 14 are formed by welding two sheets of polyurethane plastics material together. The welding may be ultrasonic welding, heat welding, infrared welding, or any other suitable and appropriate type of welding. The first sheet of plastics material has a layer of veloush material on its outer surface. The second sheet of plastics material is thicker than the first sheet of plastics material and it is positioned on the inside of the layer of plastics material of the first sheet, i.e. opposite the veloush material. The plastics material may be a urethane plastics material.

As shown in FIGS. 1 and 2, the fastener means 10 are flaps. The shaded parts of the flaps are matrices of Velcro (Registered Trade Mark) material. The fastener means 10 grips the veloush material where desired on the outside of the headwear 2, for example on the outside of the body portion 4. The fastener means 10 is easily attachable and releasable for ensuring that the headwear 2 is pulled to a tight shape which conforms best to the size and shape of the scalp of the person's head 12. With the headwear 2 being able to be used for different persons who will have different sizes and shapes of head, it is advantageous to have the fastener means such that adjustment to conform to the precise shape of the scalp of each person's head 12 is available. In addition, the fastener means 10 is easily able to be released when a treatment period is finished and it is desired to remove the headwear 2 from the person's head 12.

As shown in FIG. 1, the inlet 6 is an inlet pipe which extends beyond the periphery of the headwear 2. The outlet 8 is an outlet pipe which also extends beyond the periphery of the headwear 2.

FIGS. 2 and 3 show how the headwear 2 is able to form part of apparatus 20 for removing heat from the person's head 12 in order to prevent hair loss. As shown, the apparatus 20 comprises the headwear 2 and a pump 22 for pumping the cold fluid through the headwear 2. The apparatus 20 also comprises control means 24 for controlling the pump 22. The control means 24 maintains in use a substantially constant pressure in the headwear 2. The control means 24 includes a pressure release valve 26 and an adjustable flow restrictor 28. The control means 24 also includes a control board 30 which may be a printed circuit control board, an over pressure alarm 32, an under pressure alarm 34, and a timer 36. When the over pressure alarm 32 operates, the pipes to the headwear 2 need to be checked. When the under pressure alarm 34 operates, then the cold fluid 38 needs to be checked. The timer 36 may be an hour meter increment timer which operates when water pressure is above 4 millibars. As shown in FIG. 2, the apparatus parts 22-36 are able to be housed in a control box 40.

The apparatus 20 shown in FIGS. 2 and 3 maintains a constant pressure chosen to be in the range of 7-13 millibars, and preferably at a constant pressure of 10 millibars.

The cold fluid 38 is held in an insulated container 42. In FIG. 2 the insulated container 42 is shown with a lid 44. For simplicity of illustration, the lid 44 has not been shown in FIG. 3. As shown in FIG. 3, the insulated container 42 has an inlet diffuser 46 which operates to stop ice blocking the water pipe 48 leading to the pump 22. The pump 22 pumps the cold fluid 38 via a pipe 50 through the pressure release valve 26 and a pipe 52 to the headwear 2. Water is returned from the headwear 2, via a pipe 54, the adjustable flow restrictor 28 and a pipe 56, to the insulated container 42 for further cooling. The adjustable flow restrictor 28 may set a flow rate at 1 litre per minute at the running pressure of 14 millibars.

The apparatus 20 is electrically powered by batteries (not shown). Electrical connections are shown by connections 58, 60, 62, 64, 66. A pressure sensor 68 at the headwear 2 feeds pressure signals along connection 66 to the control board 30. The connection 58 between the pump 22 and the control board 30 provides a connection giving pulse width modulated speed control to maintain the chosen pressure of 10 millibars in the headwear 2.

As shown in FIG. 2, the apparatus 20 is mobile apparatus for being movable by the person 70. More specifically, the insulated container 42 is provided with wheels 72. The control box 40 is mounted on the insulated container 42. Thus the person 70 is able to move the entire apparatus 20 from one position to another, for example if the person 70 should wish to obtain a beverage or something else during a treatment session. Because the apparatus is battery powered, the apparatus 40 is not limited to movement which is the length of an electrical lead plugged into a socket which would be required if the apparatus were mains powered.

The apparatus 20 provides a cooling flow of cold fluid through the headwear 2. Even if the person 70 stands up or otherwise moves, the control means 24 is able to ensure that the pressure in the headwear 2 stays substantially constant. Discomfort to the person 70 caused by overpressure is avoided. Rupturing of one or more of the pouch portions 16 in the headwear 2 is also avoided if the person stands up or otherwise moves. The headwear 2 is able to prevent or reduce hair loss during chemotherapy, and thereby to provide an important psychological boost to the person 70 at a time when they need it and are being treated by the chemotherapy for cancer.

Figure 4:
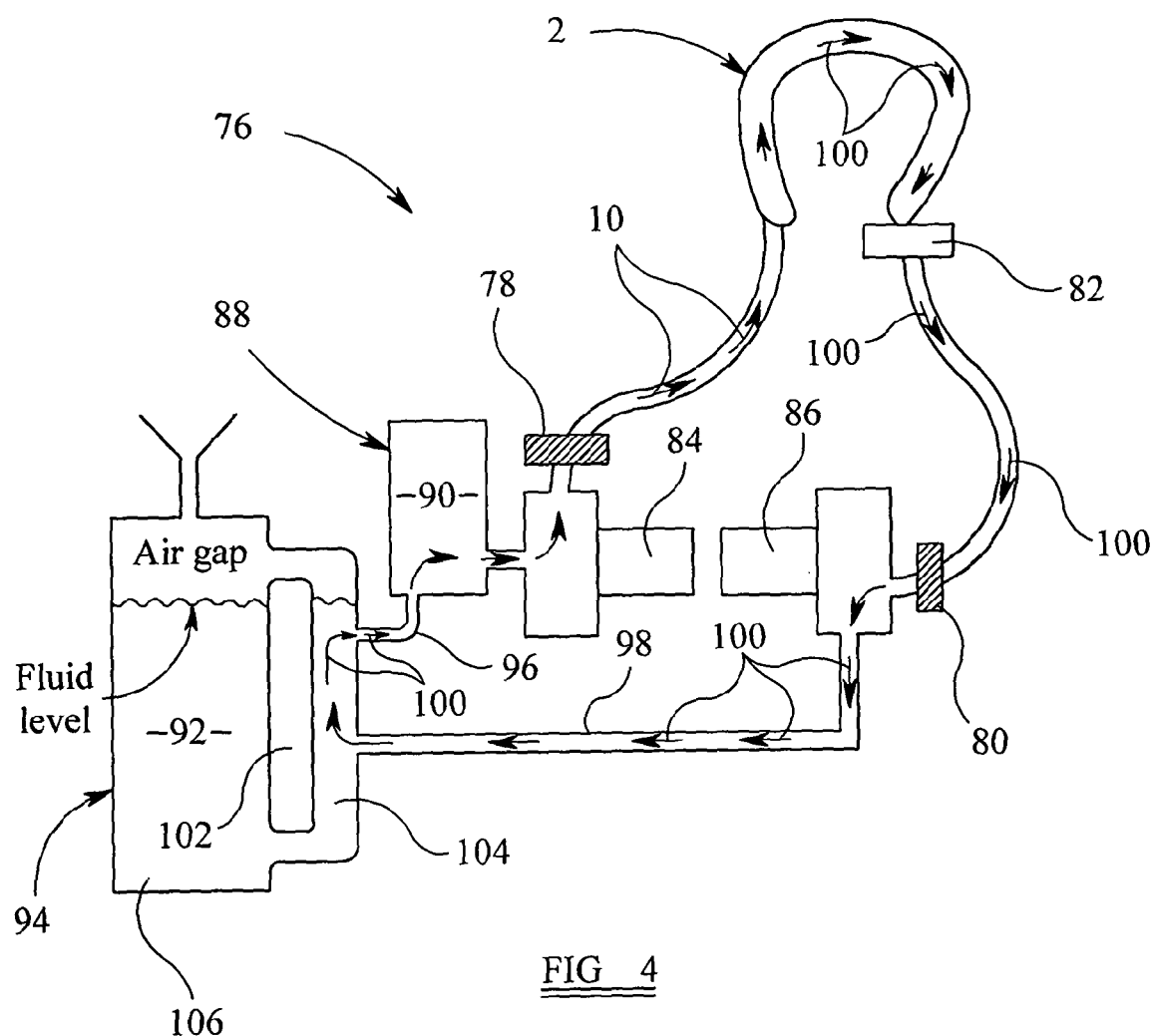
FIG. 4 illustrates the construction and operation of second apparatus.

Referring now to FIG. 4, there is shown apparatus 76 for use with the headwear 2 shown in FIG. 1. The apparatus 76 comprises an upstream temperature sensor 78, a downstream temperature sensor 80 and a pressure sensor 82. The apparatus 76 also comprises two pumps in the form of a feed pump 84 and a drain pump 86. The heat pump unit 88 includes a heat cooler unit 90. Cold fluid 92 is provided in a main tank 94. The tank 94 has an outlet pipe 96 and an inlet pipe 98. The flow of cold fluid 92 through the apparatus 76 is shown by flow arrows 100. The main tank 94 has an isolator device in the form of a panel 102. The panel 102 acts to constrain the circulating fluid 92 to the right side of the main tank 94 in an area 104. This means that the circulating cold fluid 92 does not have to circulate through the larger area 106. This thereby reduces the heating/cooling load on the pump unit 68. In operation, the feed pump 84 and the drain pump 96 are speed controlled by a microprocessor (not shown) which uses information from the temperature sensors 78, 80 and the pressure sensor 82.

The apparatus 20 shown in FIGS. 2 and 3 uses gravity to draw the cold fluid out of the headwear 2. Also, the cold fluid has to be pumped up to the headwear 2 by the pump 22. In the apparatus 76, instead of having one pump 22 as in the apparatus 20, there are two pumps, namely the feed pump 84 and the drain pump 86. The feed pump 84 acts like the pump 22 shown in FIG. 3. The drain pump 86 draws the cold fluid from the headwear 2. The difference in speed between the feed pump 84 and the drain pump 86 creates the pressure in the headwear 2. The microprocessor thus controls the pressure in the headwear 2.

The apparatus 20 shown in FIGS. 2 and 3 is such that the cold fluid is cooled with ice. In contrast, in the apparatus 76, the cold fluid is cooled using a refrigeration unit such as the illustrated heat/cooler unit 90. The refrigeration unit may be a Peltier cooler which operates using a Peltier effect. Alternatively, the refrigeration unit may be a compressor such for example as a compressor used for a refrigeration unit in a refrigerator. The refrigeration unit should preferably be such that it has a good cooling response time on the cold fluid passing through the headwear 2.

The microprocessor used with the apparatus shown in FIG. 4 is able to control pressure and temperature in cycles. The apparatus operates with a very low pressure of, for example, 0.1-0.26 psi, or approximately 7-18 millibars. With the apparatus 20 shown in FIGS. 2 and 3, the person 70 needs to hold their head 12 high, and approximately 3 feet or approximately 900 mm, above the control box 40. This is in order to provide enough height for gravity to operate and draw the cold fluid out of the headwear 2 during the operation of the apparatus 20. Also, the person 70 is preferably near the apparatus 20. With the apparatus 76, it is not necessary for the person 70 to hold their head 12 so high because the drain pump 76 operates to remove the cold fluid from the headwear 2. With the apparatus 76, the person's head 12 can be at any appropriate relative height and proximity to the apparatus 76.

It is to be appreciated that the embodiment of the invention described above with reference to the accompanying drawings has been given by way of example only and that modifications may be effected. Thus, for example, the shape of the headwear 2 may be different from that shown in FIG. 1. The size, shape and number of the pouch portions 16 may be different from those shown in FIG. 1. The size, shape and number of empty spaces 74 may be different from those shown in FIG. 1. The empty spaces 74 enable the headwear 2 to be folded easily. The empty space 75 locates over the forehead of the person's head 12 where cooling is not required because there is no hair on the forehead. The apparatus 20 may be different from that shown in FIG. 2. The cold fluid may be water, brine, or a refrigerant from a refrigeration unit. With a refrigeration unit, the refrigeration unit would usually be mains operated but with the facility of battery operation to enable a person to move to a new destination and plug back into the mains. Individual components shown in the drawings are not limited to use in their drawings and they may be used in other drawings and aspects of the invention.

The invention claimed is:

1. An apparatus for removing heat from an adult person's scalp solely in order to prevent hair loss, the apparatus comprising a one-piece item of headwear and a feed pump for pumping a cod fluid to the headwear, and wherein:
   (i) the headwear comprises a body portion for fitting over the person's scalp, en inlet for the cold fluid, an outlet for the cold fluid, and fastener flaps which comprise matrices of hook or loop material and which fold over the headwear and adjustably releasably grip parts of the headwear for fastening the headwear securely on the person's head, wherein the headwear opens to a flat condition when it is not in use on the person's head, in the flat condition the flaps extend outwardly beyond the body portion, access to the person's scalp is not provided through the body portion, and the body portion comprises a plurality of internal walls which define pouch portions, the pouch portions being connected to one another to define a passageway through the body portion from the inlet to the outlet whereby the cold fluid is able to circulate through the body portion, at least some of the pouch portions being of dissimilar shapes, the pouch portions are expandable by the cold fluid with the expansion being restricted by the folded fastener flaps whereby the pouch portions are caused in use to press against the person's scalp with a pressure which causes the body portion to be pressed into good contact with the person's scalp and thereby to facilitate maximum cold transfer from the body portion to the person's scalp, (ii) the feed pump comprises control means which is configured to operate to maintain in use a substantially constant pressure in the headwear and thereby a substantially constant pressure exerted by the headwear on the person's scalp, whereby the person wearing the headwear is able to stand up without causing a change in pressure in the headwear and resulting discomfort to the person wearing the headwear, (iii) the control means comprises a pressure sans located at the headwear, and (iv) the control means and the pressure sensor are configured such that the apparatus operates only at the substantially constant pressure and only within a pressure range of 7-18 millibars.

2. The apparatus according to claim 1 in which the head ear is formed of sheets of material, and in which the internal walls are formed by welding the sheets of material together.

3. The apparatus according to claim 2 in which there are two of the sheets, the first sheet comprising a layer of a plastics material having a layer of a grippable material on an outer surface of the layer of the plastics material, the second sheet comprising a layer of plastics material which is thicker than the layer of plastics material in the first sheet, and the two layers of the plastics material being in contact with each other.

4. The apparatus according to claim 3 in which the two layers of the plastics material are two layers of the same plastics material.

5. The apparatus according to claim 4 in which the plastics material is a urethane plastics material.

6. The apparatus according to claim 1 in which the inlet is an inlet pipe which extends beyond the periphery of the headwear, and in which the outlet is an outlet pipe which extends beyond the periphery of the headwear.

7. The apparatus according to claim 1 and including a drain pump for removing the cold fluid from the headwear.

8. The apparatus according to claim 7 in which the control means controls the drain pump.

9. The apparatus according to claim 1 in which the control means includes a pressure release valve for releasing the cold fluid from the headwear, and an adjustable flow restrictor.

10. The apparatus according to claim 1 and including an insulated container for the cold fluid.

11. The apparatus according to claim 1 in which the apparatus is a mobile apparatus for being movable by the person.

12. The apparatus according to claim 11 in which the apparatus has wheels for enabling the apparatus to be wheeled to a desired position.

13. The apparatus according to claim 1 in which the apparatus is battery powered.

14. The apparatus according to claim 1 in which the pouches are of a size such that in use the total cold fluid content of the headwear is 1.6 kg.

15. An apparatus for removing heat from an adult person's scalp solely in order to prevent hair loss, the apparatus comprising a one-piece item of headwear and a feed pump for pumping a cold fluid to the headwear, and wherein:

(i) the headwear comprises a body portion for fitting over the person's scalp, an inlet for the cold fluid, an outlet for the cold fluid, and fastener flaps which comprise matrices of hook or loop material and which fold over the headwear and adjustably releasably grip parts of the headwear for fastening the headwear securely on the person's head, wherein the headwear opens to a flat condition when it is not in use on the person's head, in the flat condition the flaps extend outwardly beyond the body portion, access to the person's scalp is not provided through the body portion, and the body portion comprises a plurality of internal walls which define pouch portions, the pouch portions being connected to one another to define a passageway through the body portion from the inlet to the outlet whereby the cold fluid is able to circulate through the body portion, at least some of the pouch portions being of dissimilar shapes, the pouch portions are expandable by the cold fluid with the expansion being restricted by the folded fastener flaps whereby the pouch portions are caused in use to press against the person's scalp with a pressure which causes the body portion to be pressed into good contact with the person's scalp and thereby to facilitate maximum cold transfer from the body portion to the person's scalp, (ii) the feed pump comprises control means which is configured to operate to maintain in use a substantially constant pressure in the headwear and thereby a substantially constant pressure exerted by the headwear on the person's scalp, whereby the person wearing the headwear is able to stand up without causing a change in pressure in the headwear and resulting discomfort to the person wearing the headwear, (iii) wherein the apparatus includes a drain pump for removing the cold fluid from the headwear, (iv) the control means controls the drain pump, (v) the control means includes a pressure release valve for releasing the cold fluid from the headwear, and an adjustable flow restrictor, (vi) the control means comprises a pressure sensor located at the headwear, and (vii) the control means and the pressure sensor are configured such that the apparatus operates only at the substantially constant pressure and only within a pressure range of 7-18 millibars.

16. An apparatus for removing heat from an adult person's scalp solely in order to prevent hair loss, the apparatus comprising a one-piece item of headwear and a feed pump for pumping a cold fluid to the headwear, and wherein:

(i) the headwear comprises a body portion for fitting over the person's scalp, an inlet for the cold fluid, an outlet for the cold fluid, and fastener flaps which comprise matrices of hook or loop material and which fold over the headwear and adjustably releasably grip parts of the headwear for fastening the headwear securely on the person's head, wherein the headwear opens to a flat condition when it is not in use on the person's head, in the flat condition the flaps extend outwardly beyond the body portion, access to the person's scalp is not provided through the body portion, and the body portion comprises a plurality of internal walls which define pouch portions, the pouch portions being connected to one another to define a passageway through the body portion from the inlet to the outlet whereby the cold fluid is able to circulate through the body portion, at least some of the pouch portions being of dissimilar shapes, the pouch portions are expandable by the cold fluid with the expansion being restricted by the folded fastener flaps whereby the pouch portions are caused in use to press against the person's scalp with a pressure which causes the body portion to be pressed into good contact with the person's scalp and thereby to facilitate maximum cold transfer from the body portion to the person's scalp, (ii) the feed pump comprises control means which is configured to operate to maintain in use a substantially constant pressure in the headwear and thereby a substantially constant pressure exerted by the headwear on the person's scalp, whereby the person wearing the headwear is able to stand up without causing a change in pressure in the headwear and resulting discomfort to the person wearing the headwear, (iii) the apparatus includes a drain pump for removing the cold fluid from the headwear, (iv) the control means controls the drain pump, (v) the control means includes a pressure release valve for releasing the cold fluid from the headwear, and an adjustable flow restrictor, (vi) the control means comprises a pressure sensor located at the headwear, (vii) the control means and the pressure sensor are configured such that the apparatus operates only at the substantially constant pressure and only within a pressure range of 7-18 millibars, (viii) the apparatus includes an insulated container for the cold fluid, (ix) the apparatus is a mobile apparatus having wheels for enabling the apparatus to be wheeled to a desired position, and (x) the total fluid content of the head ear is 1.6 kg.

* * * * *